US008258450B1

(12) United States Patent
Fries

(10) Patent No.: US 8,258,450 B1
(45) Date of Patent: Sep. 4, 2012

(54) PHYSICAL AND CHEMICAL INTEGRATED FLOW IMAGING DEVICE

(75) Inventor: David Fries, St. Petersburg, FL (US)

(73) Assignee: University of South Florida, Tampa, FL (US)

(*) Notice: Subject to any disclaimer, the term of this patent is extended or adjusted under 35 U.S.C. 154(b) by 209 days.

(21) Appl. No.: 12/505,059

(22) Filed: Jul. 17, 2009

Related U.S. Application Data

(63) Continuation of application No. 12/492,789, filed on Jun. 26, 2009, now abandoned.

(60) Provisional application No. 61/075,803, filed on Jun. 26, 2008.

(51) Int. Cl.
*H01L 29/66* (2006.01)
*G01N 27/00* (2006.01)
(52) U.S. Cl. ................................. 250/208.1; 257/414
(58) Field of Classification Search ................ 250/208.1; 257/414
See application file for complete search history.

(56) References Cited

U.S. PATENT DOCUMENTS

| | | | | |
|---|---|---|---|---|
| 5,170,127 A * | 12/1992 | Henley | ............................ | 324/658 |
| 5,890,095 A * | 3/1999 | Barbour et al. | ................. | 702/40 |
| 5,911,872 A * | 6/1999 | Lewis et al. | .................... | 205/787 |
| 5,951,846 A * | 9/1999 | Lewis et al. | .................... | 506/12 |
| 5,959,191 A * | 9/1999 | Lewis et al. | .................... | 73/31.05 |
| 6,010,616 A * | 1/2000 | Lewis et al. | .................... | 205/787 |
| 6,093,308 A * | 7/2000 | Lewis et al. | .................... | 205/787 |
| 6,483,096 B1 * | 11/2002 | Kunz et al. | ................. | 250/214 R |
| 7,091,726 B2 * | 8/2006 | Sano et al. | ..................... | 324/661 |
| 7,119,553 B2 * | 10/2006 | Yang et al. | ..................... | 324/663 |
| 7,295,019 B2 * | 11/2007 | Yang et al. | ..................... | 324/663 |
| 7,425,749 B2 * | 9/2008 | Hartzell et al. | ............... | 257/414 |
| 7,812,622 B1 * | 10/2010 | Sun | ............................... | 324/707 |
| 2003/0193429 A1 * | 10/2003 | Campana et al. | ............... | 342/22 |
| 2005/0088185 A1 * | 4/2005 | Sano et al. | ..................... | 324/661 |
| 2006/0176062 A1 * | 8/2006 | Yang et al. | ..................... | 324/663 |
| 2007/0023851 A1 * | 2/2007 | Hartzell et al. | ............... | 257/414 |
| 2007/0159185 A1 * | 7/2007 | Yang et al. | ..................... | 324/663 |
| 2008/0079421 A1 * | 4/2008 | Jensen | ..................... | 324/207.17 |
| 2008/0204713 A1 * | 8/2008 | Indermuehle et al. | .......... | 356/72 |

FOREIGN PATENT DOCUMENTS

WO 2007037926 A2 4/2007

OTHER PUBLICATIONS

Park et al., An MOS Switched-Capacitor Readout Amplifier for Capacitive Pressure Sensors, Proc. IEEE Custom Integrated Circuits Conference, May 1983, pp. 380-384.
Markus et al., MEMS: A Closer Look Part 1: Proliferation and Promise, Sensors, 1996, pp. 4-7.
Bryzek, MEMS: A Closer Look Part 2: The MEMS Industry in Silicon Valley and Its Impact on Sensor Technology, Sensors, 1996, pp. 4, 6, 8, 9, and 38.

(Continued)

*Primary Examiner* — John Lee
(74) *Attorney, Agent, or Firm* — Robert J. Varkonyi; Smith & Hopen, P.A.

(57) ABSTRACT

The device allows imaging of the flow of proximity multi environmental parameters, like temperature, pressure, force, while simultaneously detecting environmental molecules/chemicals. The device may be housed in a portable camera-like or sheet detection system. Such a system will allow the real time visualization of the chemistry and physics of fluids (air, water, plasmas) in a camera format and create a novel environmental monitoring system.

18 Claims, 9 Drawing Sheets

OTHER PUBLICATIONS

Hogenbirk et al., An Integrated Smart Sensor for Flow and Temperature with I2C Bus Interface: FTS2, IEEE, 1995, pp. 2225-2228.
Koomen, Technologies for the Multimedia City, Proceedings of the 25th European Solid State Device Research Conference, Sep. 1995, pp. 25-36.
Huijsing, Integrated Smart Sensors, Sensors and Actuators A, 1992, vol. 30, Nos. 1 and 2, pp. 167-174.
Bult et al., Wireless Integrated Microsensors, Solid-State Sensor and Actuator Workshop, Jun. 1996, Hilton Head, South Carolina, pp. 205-210.
Minakami et al., Research and Development of the "Intelligent Data Carrier", 6th World Congress on Intelligent Transport Systems, 1999, Toronto, Canada, pp. 1-10.
Yazdi et al., A Low-Power Generic Interface Circuit for Capacitive Sensors, Digital Solid-State Sensor and Actuator Workshop, Hilton Head, SC, Jun. 1996, pp. 215-218.
Fujita, et al., Wireless MEMS Sensing System for Human Activity Monitoring, IEEE/ICNE International Conference on Complex Medical Engineering, 2007, pp. 416-420.
Fujita, et al., Integrated Multi-Environmental Sensing-System for the Intelligent Data Carrier, Sensors and Actuators A, 2002, vol. 97-98, pp. 527-534.
Fang, et al., Integrated Temperature and Humidity Sensor Based on MEMS, International Conference on Information Acquisition, 2004, pp. 84-87.
Mason, et al., A Generic Multielement Microsystem for Portable Wireless Applications, Proceedings of the IEEE, 1998, vol. 86, No. 8, pp. 1733-1746.
Chadrakasan, et al., Low-Power CMOS Digital Design, IEEE Journal of Solid-State Circuits, 1992, vol. 27, No. 4, pp. 473-484.
Wise, Device and Technology Challenges for Integrated Sensors, Proc. Eur. Soloid-State Devices, 1995, pp. 4-5.
Meindl, Low Power Microelectronics: Retrospect and Prospect, Proceedings of the IEEE,1995, vol. 83, pp. 619-635.
Abidi, Low-Power Radio-Frequency IC's for Portable Communications, Proceedings of the IEEE, 1995, vol. 83, pp. 544-569.
Vittoz, et al., A Low-Voltage CMOS Bandgap Reference, IEEE Journal of Solid-State Circuits, 1979, vol. SC-14, No. 3, pp. 573-577.
Zhang, et al., A High-Accuracy Multi-Element Silicon Barometric Pressure Sensor, The 8th International Conference on Sensors and Actuators, 1995, pp. 608-611.
Chavan, et al., A Batch-Processed Vacuum-Sealed Capacitive Pressure Sensor, International Conference onSolid-State Sensors and Actuators, 1997, pp. 1449-1452.
Mason, et al., A Low-Power Wireless Microinstrumentation System for Environmental Monitoring, The 8th International Conference on Solid-State Sensors and Actuators, 1995, pp. 107-110.
Yoon, et al., An Integrated Mass Flow Sensor with On-Chip CMOS Interface Circuitry, IEEE Transactions on Electron Devices, 1992, vol. 39, No. 6, pp. 1376-1386.
Baltes, et al., Smart Sensor Interfaces, IEEE, 1996, vol. 4, pp. 380-383.
Nguyen, et al., Micromachined Devices for Wireless Communications, Proceedings of the IEEE, vol. 86, No. 8, pp. 1756-1768.
Wise, Microelectromechanical Systems: Interfacing Electronics to a Non-Electronic World, IEEE, 1996, vol. 96, pp. 11-18.
Sony.Net, Sony Global—Technology—"Exmor R", http://www.sony.net/SonyInfo/technology/technology/theme/exmore_r_01.html, Accessed on Apr. 2, 2012.

* cited by examiner

PHYSICAL AND CHEMICAL INTEGRATED FLOW IMAGING DEVICE

CROSS REFERENCE TO RELATED APPLICATIONS

This application is a continuation of U.S. application Ser. No. 12/492,789, entitled "Physical and Chemical Integrated Flow Imaging Device", filed Jun. 26, 2009, which claims priority to claims priority to U.S. Provisional Patent Application 61/075,803, entitled "Physical and Chemical Integrated Flow Imaging System", filed Jun. 26, 2008, the contents of which are herein incorporated by reference.

FIELD OF INVENTION

This invention relates to environmental sensors. Specifically, the invention discloses multiparameter pixel sensor devices for environmental testing and/or analysis.

BACKGROUND OF THE INVENTION

Recently, sensing of the various condition of the given environment is very important technology for the numerous fields (A. Mason, et al., A generic multi-element microsystem for portable wireless applications", Proc. IEEE 86 (1998) 8). Many applications of the miniaturized environmental-multi-sensor with data logging/transfer system are considerable, such as the intelligent data carrier (IDC) system, monitoring of a working condition, management of a rent-a-car insurance, safety-security, process control, scientific experimentation, and environmental testing and analysis. Especially, for any transportation system managing the logistics condition during transportation such as number, location timing, route and weather information, etc. are essential to obtain security, safety and cost minimization. However, the present logistics system is not enough to adapt the next generation data carrier. Small and lightweight IDC, which has multi-sensors and data logging processor, monitors physical circumference conditions what happened to the cargo or goods during the transportation (H. Minakami, et al. "Research and development of the intelligent data carrier" Proc. 6th World Conference on Intelligent Transaction Systems, ITSA-003052, Toronto, CN, 8-12 Nov. 1999). So far, this type of monitored information has not been available, unless using specially made expensive and large sized device.

Driven by rapid advances in microcomputers and global connectivity, many of the most important emerging markets for microelectronics require the ability to gather information from the nonelectronic world (J. H. Huijsing, "Integrated smart sensors," Sensors Actuators A, vol. 30, nos. 1/2, pp. 167-174, 1992; K. D. Wise, "Microelectromechanical systems: Interfacing electronics to a nonelectronic world," in Dig. IEEE Int. Electron Device Meeting, December 1996, pp. 11-18.). Examples include health care (diagnostic and therapeutic devices, prosthetics), automotive systems (smart vehicles and smart highways), automated manufacturing—including smart very-large-scale integration (VLSI) process tools-, environmental monitoring and control devices, defense systems, and many consumer products. Using integrated circuit technology and extensions of it, integrated sensors and microactuators are being developed to provide the necessary input/output (I/O) devices. These are increasingly being realized combined with hybrid or monolithic circuitry on a common substrate (J. Bryzek, "MEMS: A closer look," Sensors Mag., pp. 4-9, July 1996; L. Spangler and C. J. Kemp, "A smart automotive accelerometer with on-chip airbag deployment circuits," in Dig. Solid-State Sensor and Actuator Workshop, Hilton Head Island, S.C., June 1996, pp. 211-214; H. Baltes, et al., "Smart sensor interfaces," in Dig. IEEE Int. Symp. Circuits and Systems, Atlanta, Ga., May 1996, vol. 4, pp. 380-383; E. Yoon and K. D. Wise, "An integrated mass flow sensor with on-chip CMOS interface circuitry," IEEE Trans. Electron Devices, vol. 39, pp. 1376-1386, June 1992.) and have come to be known as microelectromechanical systems (MEMS). Merging these devices with increasingly powerful digital signal-processing electronics now makes it possible to go beyond simple analog readout circuitry and form complete closed-loop microsystems in very small, highly integrated modules. These autonomous microsystems are capable of gathering data from the physical world, converting them to electronic form, compensating them for interfering variables and nonlinearities, and either acting on the information directly or transferring it to other systems (S. Middlehoek and S. A. Audet, Silicon Sensors. London, UK: Academic, 1989; K. D. Wise, "Integrated microsystems: Device and technology challenges," in Proc. Eur. Solid-State Device Res. Conf. (ESSDERC), The Hague, The Netherlands, September 1995, pp. 15-24; A. Mason, N. Yazdi, K. Najafi, and K. Wise, "A low-power wireless microinstrumentation system for environmental monitoring," in Dig. Int. Conf. Sensors and Actuators (Transducers '95), Stockholm, Sweden, June 1995, pp. 107-110).

Currently, no system exists for the real time visualization of the chemistry and physics of fluids, such as air, water, and plasma, in a camera format and create a novel environmental monitoring system. Therefore, an inexpensive, but highly efficient, two dimensional or three dimensional environmental sensor which produces more reliable environmental information is needed.

SUMMARY OF THE INVENTION

The invention addresses how to image the flow of proximity multi environmental parameters (temp, pressure, force etc. . . . and simultaneously molecules/chemicals) in a portable camera like detection system. The invention is a novel multisensory pixel to enable an enhanced IDC. Such a system allows real-time visualization of the chemistry and physics of fluids (air, water, plasma) in a camera format, and creates a novel environmental monitoring system that could be used in a vast number of markets such as safety-security, process control and scientific and environmental markets. Thus, we propose a new concept IDC system.

The multiparameter sensor device is comprised of a control module and at least two sensor elements fused together, thereby forming a multisensory pixel. The control module is in electrical communication with the multisensory pixel, and may provide command signals, such as activating and deactivating the multisensory pixel. In addition, sensor signals are relayed from the multisensory pixel to the control module. In specific embodiments, the control module is made of a microcontrol unit and input/output interfaces. The control module may also include a power management module and/or system memory.

The multisensory pixels are disposed on an imaging panel array, oriented such that one face of the multisensory pixel is exposed to environmental analytes. The system is based on an array of mixed sensing elements in a rigid or flexible electronic sheet format that are made to sense multiple physical and/or chemical parameters in proximity In certain embodiments, the imaging panel array is a flexible printed electronics board or a printed circuit board micro-electro-mechanical systems board. The flexible imaging sensor array is connected to support and control electronics with data storage and display to enable a full physical and chemical integrated flow imaging system. In specific embodiments, the multisensory pixels comprise at least two fused sensors, which may be an electrochemical sensor, ion selective electrode, ion detector, polymer sensor, chemical field-effect transistor, chemical sensitive membrane, antibody, luminescent reaction sensor, surface Plasmon element, regenerative reactive sensor, regenerative sense sensor, complementary metal-oxide-semiconductor, surface-on-insulator, liquid crystal polymer, or capacitive sensor. The sensors may be used to sense environmental conditions such as temperature, pressure, microbalance, force, humidity, acceleration, and chemical characteristics. In some embodiments, the system uses flexible printed electronics and printed circuit board-micro-electro-mechanical systems (PCB-MEMS). PCB-MEMS, and flexible printed circuits may be used to fabricate multi sensor elements or "pixels".

The sensor device also optionally includes a battery in electrical communication with the control module and multisensory pixel. Additionally, some embodiments also possess a transceiver in electrical communication with the input/output interfaces of the control module. The transceiver used may be a complementary metal-oxide-semiconductor, silicon bipolar, silicon/silicon-germanium heterojunction bipolar transistor, or GaAs MESFET.

In some embodiments, an image sensor is used to convert an optical image focused on the sensor into electrical signals. The image sensor typically includes an array of light detecting elements, where each element produces a signal corresponding to the intensity of light impinging on that element when an image is focused on the array. These signals may then be used, for example, to display a corresponding image on a monitor or otherwise used to provide information about the optical image. Exemplary image sensors include charge coupled device (CCD) and (CMOS). Integrated circuit chips containing a CCD image sensor have a relatively low yield and are expensive due to the specialized processing involved.

The multi parameter pixel is a fusion of individual sensor elements into a multi sensory pixel that can be arrayed into imaging panels of any size. The pixels can be ganged together into an array and outfitted with standard systems electronics into a camera system. Alternatively, the imaging array may be a "skin" or conformal imaging sheets on structures.

The system allows the real time visualization of the chemistry and physics parameter makeup of fluids (air, water, plasmas) in a camera format that could be used in a wide variety of environments and investigations. It allows monitoring of chemicals, biological signatures, and physical detection over a large area of the environment.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

Disclosed herein is a multi-environmental data monitoring system. Capacitive sensors may be utilized in the device, as these sensors offer high sensitivity yet consume no power and can be read out rapidly using low-power circuit techniques. The system may provide physical sensing for local environmental conditions, including, without limiting the scope of the invention, temperature, pressure microbalance, force, humidity, acceleration; and chemical sensing. Useful chemical sensor may comprise electrochemical, ion selective electrode, ion detector, polymer sensors, chemical field-effect transistor (chemFETs), chemical sensitive membranes, antibody, luminescent reaction chemistries, surface Plasmon elements, regenerate reactive/sense surfaces, discrete sensor chips, and any combination thereof. In some embodiments, the interface circuitry is designed to operate with low power consumption. The multi-environmental sensory device uses an array of MEMS sensors fused into multisensor pixels and discrete electronic components.

As used in this paper, a "microsystem" is defined as a collection of highly integrated devices that contains transducers along with appropriate interface circuitry and is capable of performing multiple tasks autonomously as well as responding intelligently to various commands from a host system.

The multisensor pixel device is useful for environmental monitoring, including without limitation, use as a microweather station for local, regional, and global weather forecasting. The multisensor pixels consists of the sensing part with the MEMS sensors, controlled by a microcontrol unit (MCU) that comprising a microprocessor for signal processing, stored-program control, and I/O interfaces. Wireless embodiments of the device also comprise a power-management unit. Adequate on-chip read-only memory (ROM), random-access memory (RAM), and electrically erasable and programmable (EEP) ROM are important in selecting an MCU. Exemplary microprocessors for use in the MCU include PIC16LF877 (Microchip Technology Inc., Chandler, Ariz.) and 68HC11 (Motorola, Inc., Holtville, N.Y.). In some embodiments, the microprocessor has low power consumption of about 10 mW active; 20 W standby.

Low power, low-voltage circuit techniques (A. Chandrakasan, et al., "Low-power CMOS digital design," *IEEE J. Solid-State Circuits*, vol. 27, pp. 473-484, April 1992) should be used along with the smallest possible device dimensions to help reduce load capacitances. The ability to shut down MCU subsystems selectively when not in use can further reduce power dissipation. Last, the ability to programmably control clock frequencies would allow transducer front-end operations to occur more slowly while processing data at the fastest possible rate.

Figure 1:
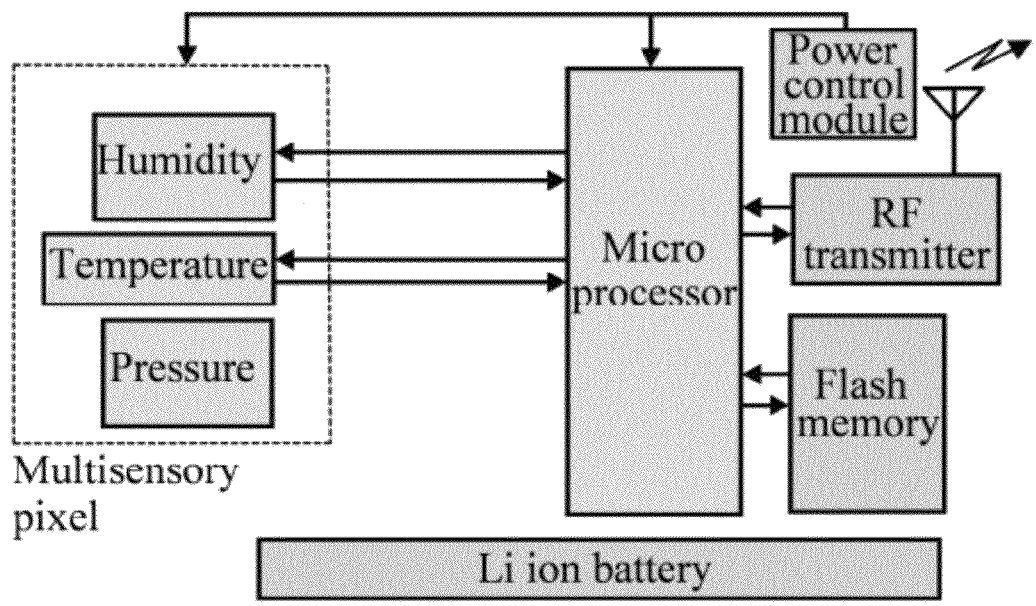
FIG. 1 is a block diagram showing an embodiment of the environmental sensor device for remote detection.

The device may be used in remote locations, such as underwater monitoring. In such cases, a single-cell or multi-cell Li-ion battery and linear voltage regulator with 3V DC supply serve as system power. FIG. 1 shows a block diagram of the monitoring device, comprising the multi-sensor pixels and a microprocessor unit (MCU). The device may continuously monitor environmental conditions or acquire data at discrete, intermittent time points to reduce power consumption. In intermittent data collection, the device is typically inactive, except for a power-management chip (PMC). Exemplary PMCs include complementary metal-oxide-semiconductor (CMOS) circuitry that can implement all of the necessary functions with less than 10 A of supply current. Discrete sensors may be powered up and down by a voltage reference controlled by the PMC that are controlled by input codes sent from the MCU. During acquisition mode, the sensors are activated and sensor signals and peak values sequentially recorded into the system memory, such as flash memory. The output data from the sensors are transferred to the microprocessor by analog and digital signals, and then stored in the flash memory or transmitted via the RF module or wire communications.

Radio frequency (RF) technology has moved from purely analog to a mix of analog and digital components, providing a more efficient use of bandwidth, lower power dissipation, and improved noise immunity (L. E. Larson, *RF and Microwave Circuit Design for Wireless Communications*. Norwood, Mass.: Artech House, 1996). Several technologies are useful as RF transceivers include, without limiting the scope of the invention, CMOS, Si bipolar, Si/SiGe heterojunction bipolar transistors (HBT's), and GaAs MESFET and HBT devices. The passive components (inductors, capacitors, filters, and resonators) used often determine the size and performance of such systems, and use of MEMS allow manufacture of the transceiver monolithically, reducing size, weight, cost, and power (C. T.-C. Nguyen, et al., "Micromachined devices for wireless communications," *Proc. IEEE*, this issue, pp. 1756-1768). Likewise, low-power CMOS wireless systems may be utilized (K. Bult, et al., "Wireless integrated microsensors," in *Dig. Solid-State Sensor and Actuator Workshop*, Hilton Head, S.C., June 1996, pp. 205-210). For wireless operation, it is important to use low power telemetry hardware, understanding the direct tradeoff between power and communication range. While many efforts are currently under way to reduce the power consumption of the sensors, control circuitry (J. D. Meindl, "Low power microelectronics: Retrospect and prospect," *Proc. IEEE*, vol. 83, pp. 619-635, April 1995) and wireless communication devices (A. A. Abidi, "Low-power radio-frequency IC's for portable communications," *Proc. IEEE*, vol. 83, pp. 544-569, April 1995), system-level approaches to power management are also important. An accepted method for conserving power is to power down unused subsystems. The PMC may also control by transmission activity of the RF transmitter, shutting the transmitter off by commands from the MCU. Thus, the MCU, through the PMC, controls when and where power is available.

A multisensor pixel system is arranged as an array, which analyze physical sensing temperature, pressure microbalance, force, humidity, acceleration; and chemical sensing. Useful chemical sensor may comprise electrochemical, ion selective electrode, ion detector, polymer sensors, chemical field-effect transistor (chemFETs), chemical sensitive membranes, antibody, luminescent reaction chemistries, surface Plasmon elements, regenerate reactive/sense surfaces, discrete sensor chips, and any combination thereof. Exemplary sensors are discussed, which serve as examples only and are not intended to limit the scope of the invention.

Figure 2:
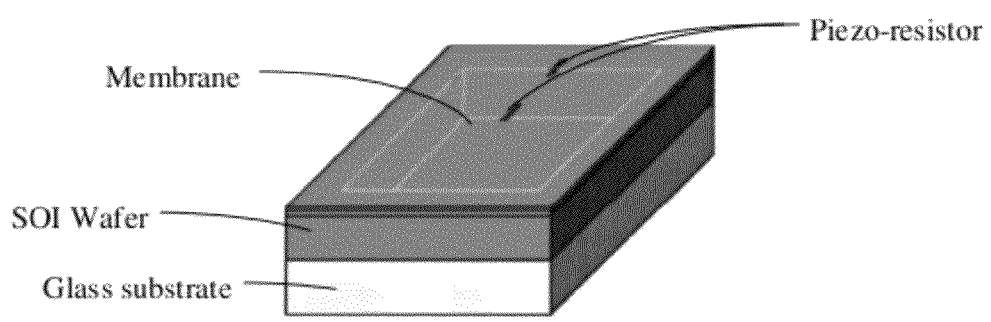
FIG. 2 is an illustration showing the structure of an exemplary SOI pressure sensor.

A silicon-on-insulator (SOI) is used as a pressure sensor, seen in FIG. 2. The active layer of the SOI wafer forms the thin diaphragm with area of 2.5 mm$^2$ and thickness of 25 µm, and it form the vacuum chamber with the glass substrate, as shown in FIG. 2. The piezo-resistors placed on the diaphragm and fixed part of the wafer form a full bridge and provide the voltage output according to the induced strain form ambient pressure. The peripheral circuitry is same as the one of the accelerometer, which has low power consumption and dynamic offset adjustment mechanism. The thermal compensator can be realized by the microprocessor.

Figure 3:
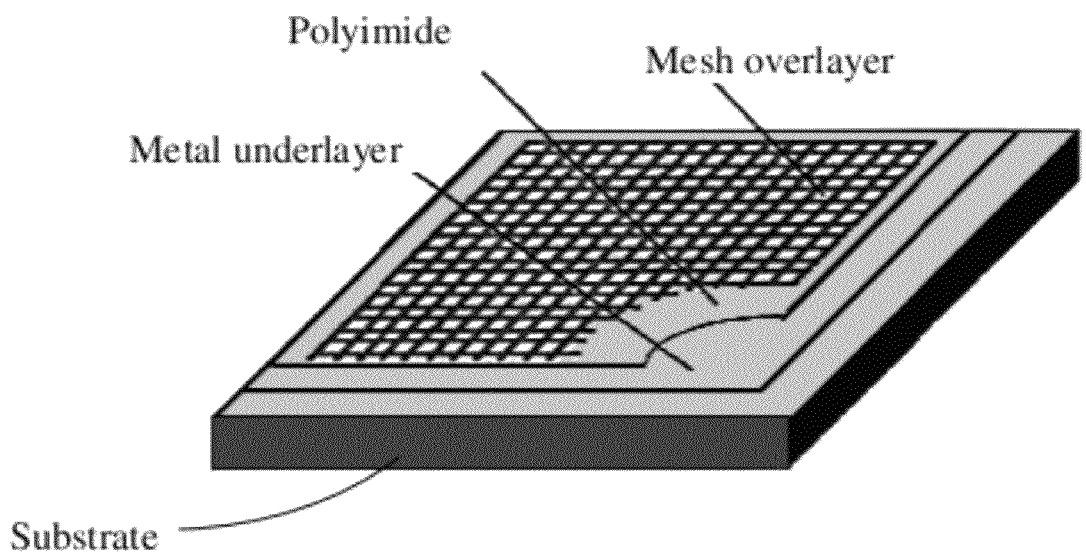
FIG. 3 is (A) an illustration showing the structure of an exemplary polyimide humidity detector; and (B) a schematic diagram of the polyimide humidity detector.
Figure 3:
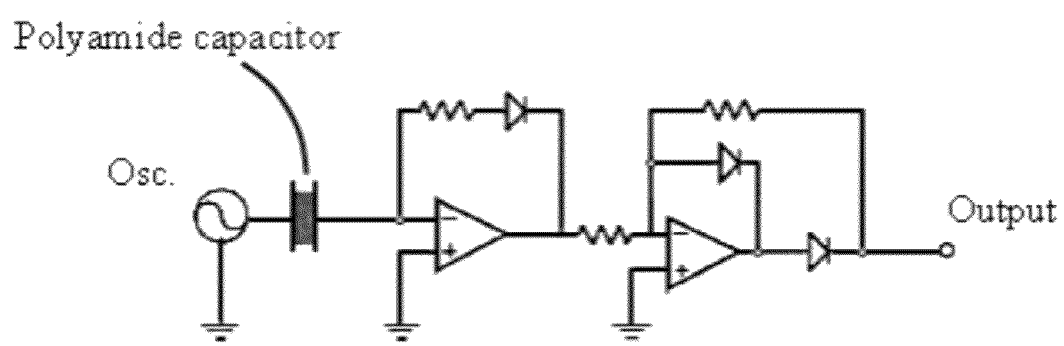

A humidity sensor may be constructed, the structure of humidity sensor and its peripheral circuitry seen in FIG. 3. The sensor was composed of polyimide film as a moisture absorbent. Since the impedance of the polyimide film decreases almost exponentially with humidity, a log circuit and oscillator used to measure impedance, which correlates to the humidity. The fabrication of polyimide film for moisture absorption is compatible with the two-layer aluminum interconnection process.

Figure 4:
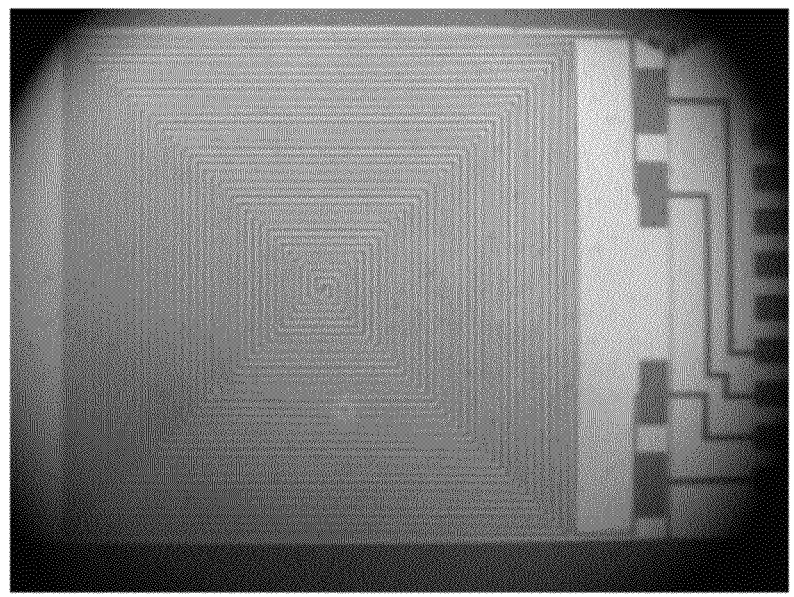
FIG. 4 is an image showing the PCB MEMS-based temperature sensor.

To measure temperature in close proximity to the other sensors in the microsystem, a temperature sensor has been integrated on the interface chip, seen in FIG. 4. This sensor provides data that can be used to compensate digitally for the temperature sensitivity of any other sensors connected through this chip. The temperature sensor utilizes the temperature dependence of the drain current of an CMOS transistor in weak inversion (E. Vittoz and O. Neyroud, "A low-voltage CMOS bandgap reference," *IEEE J. Solid-State Circuits*, vol. SC-14, pp. 573-577, June 1979). The charging current for the capacitively loaded Schmitt input stage of a ring oscillator is set by a p-channel MOS transistor biased for sub-threshold operation. Since this charging current is temperature dependent, the frequency of the oscillator provides a measure of the local temperature. A typical device displays a sensitivity of 4 ms/° C. at 60° C. and 33 ms/C at 20 C with a resolution better than 0.5° C. across the tested range. Although the sensor is highly nonlinear, it is easily calibrated using the digital techniques, provides a direct digital output and very low power dissipation, and can easily be implemented in a standard CMOS process.

Figure 5:
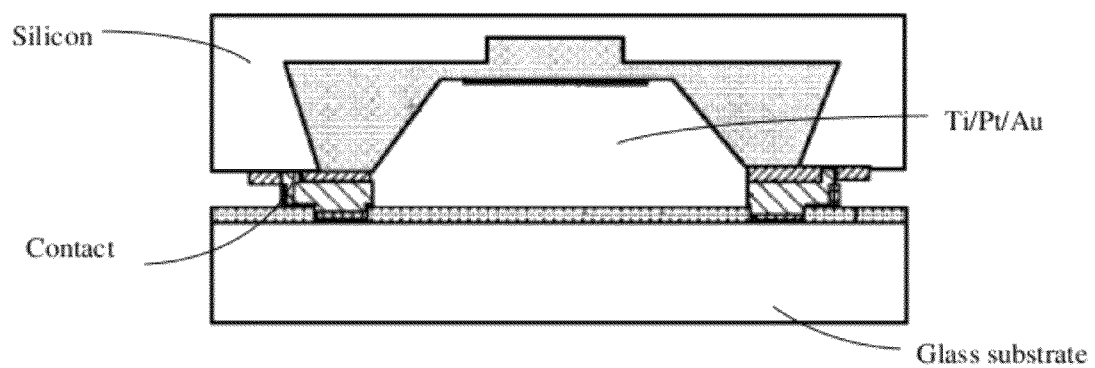
FIG. 5 is an illustration of the structure of an exemplary capacitive barometric sensor.

Barometric sensors functional at between 20 and 60° C. and 600 to 800 torr were developed for use in close proximity to the other sensors. The targeted resolution of 25 mtorr here is equivalent to about one foot of altitude shift at sea level. To achieve wide dynamic range and high resolution simultaneously, a multitransducer vacuum-sealed capacitive pressure sensor has been developed (Y. Zhang and K. D. Wise, "A high-accuracy multi-element silicon barometric pressure sensor," in *Dig. Int. Conf. Sensors and Actuators (Transducer'95)*, Stockholm, Sweden, June 1995, pp. 608-611; A. V. Chavan, and K. D. Wise, "A batch-processed vacuum sealed capacitive pressure sensor," in *Dig. Int. Conf. Solid-State Sensors and Actuators (Transducers'97)*, Chicago, Ill., June 1997, pp. 1449-1452). This device uses multiple diaphragms to segment the overall pressure range, as shown in FIG. 5. The sensor is fabricated using bulk micromachining and a silicon-glass dissolved-wafer process (A. V. Chavan, and K. D. Wise, "A batch-processed vacuum sealed capacitive pressure sensor," in *Dig. Int. Conf. Solid-State Sensors and Actuators* (*Transducers'97*), Chicago, Ill., June 1997, pp. 1449-1452). To measure barometric pressure, the microcontroller first reads out the smallest of the diaphragms, which serves as a global sensor spanning the entire measurement range at relatively low resolution. After determining the approximate pressure, the controller then selects the appropriate segment transducer. The diaphragm deflection varies with increasing pressure according to the fourth power of its diameter, causing the largest of the diaphragms to approach the glass first. As the gap approaches zero, a very high pressure sensitivity is achieved. The transducer capacitance is read using the switched-capacitor charge integrator on the interface chip.

Figure 6:
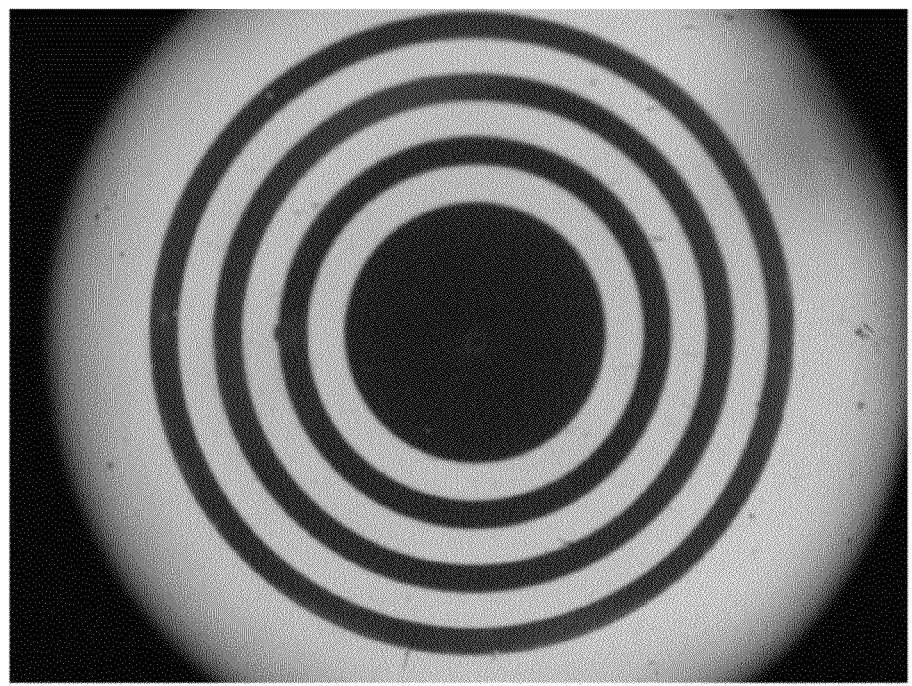
FIG. 6 depicts the PCB MEMS-based planar LCP conductivity cell.
Figure 7:
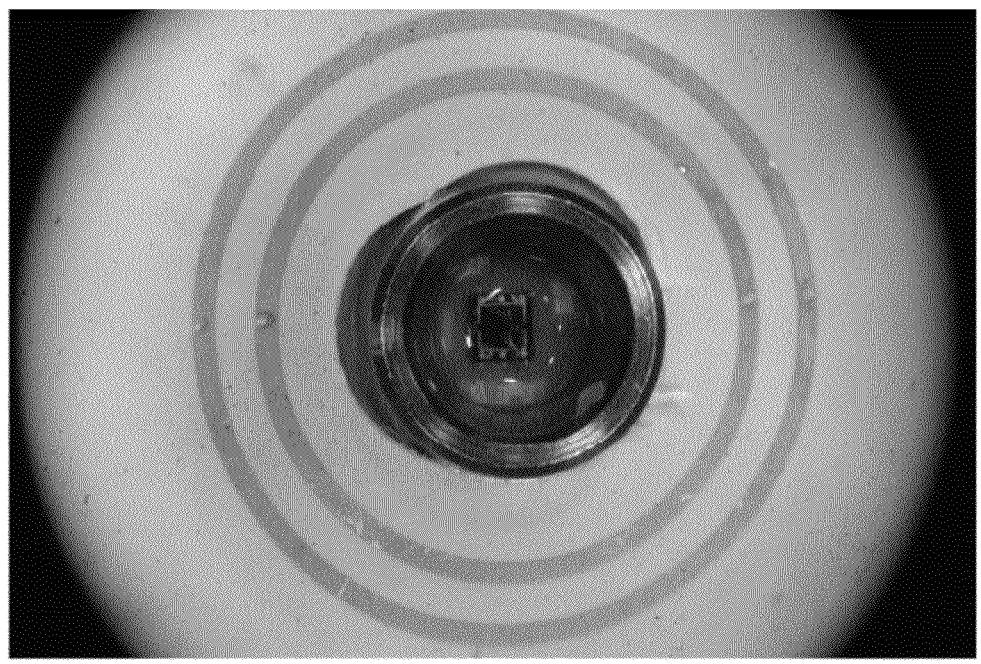
FIG. 7 depicts a coarse example of a multisensor pixel formed from a combined C-T-P pixel element on flex PCB based planar LCP, conductivity cell on LCP with a pressure and temperature chip in the middle. Sensors can be discrete or integrated into the flex substrate.
Figure 8:
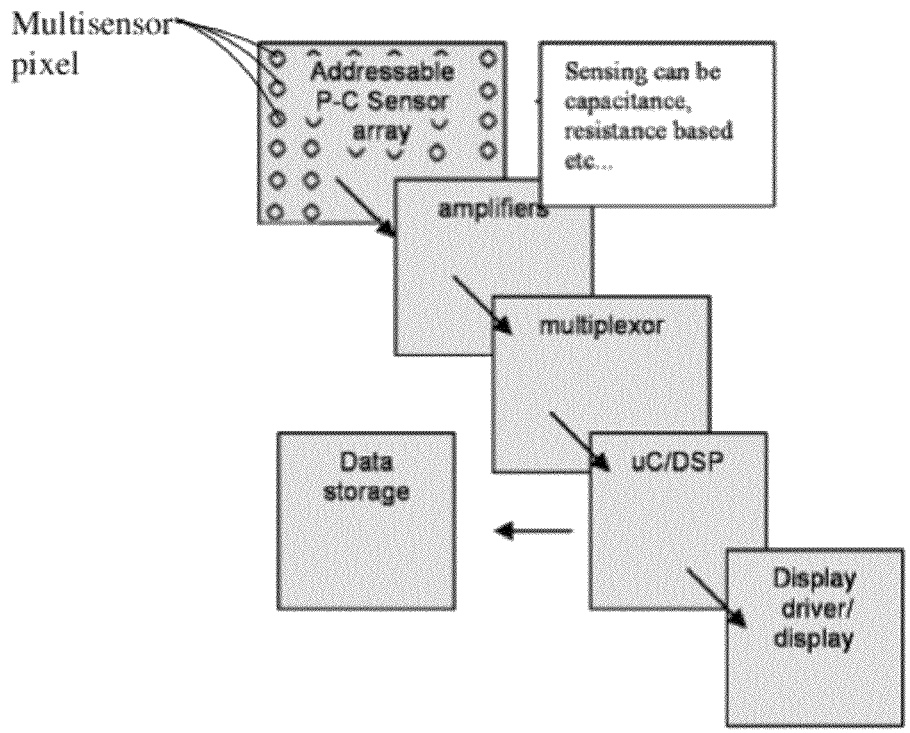
FIG. 8 depicts a block diagram of the camera system. The circular members represent individual multisensor pixels.

Sensor elements such as the PCB MEMS-based liquid crystal polymer (LCP) conductivity cell seen in FIG. 6, and temperature sensor are employed in creating multiple sensor elements for the device. The "pixels" of the sensor are a fusion of individual sensor elements, seen in FIG. 7, creating a multi-sensory pixel that can be arrayed into imaging panels of any size. The multi-sensory pixels can be arranged to form an array and outfitted with standard system electronics to create a camera system. In some embodiments, imaging pixels are used in combination with the environmental pixels of the present invention. Exemplary imaging pixels are known in the art, and may be formed as CMOS pixels. In such a CMOS type image sensor, a photodiode or phototransistor, or other suitable device, is used as the light detecting element, where the conductivity of the element corresponds to the intensity of light impinging on the element. The variable signal thus generated by the light detecting element is an analog signal whose magnitude is approximately proportional (within a certain range) to the amount of light impinging on the element. It is known to form these light detecting elements in a two dimensional core array which is addressable by row and column Once a row of elements has been addressed, the analog signals from each of the light detecting elements in the row are coupled to the respective columns in the array. An analog-to-digital (A/D) converter may then be used to convert the analog signals on the columns to digital signals so as to provide only digital signals at the output of the image sensor chip. FIG. 8 depicts the development of such a camera system. Alternatively, the imaging array can be a "skin" of sensor arrays, for example a conformal imaging sheet. In the imaging sheet, the sensors are addressed or scanned, yielding an image of both the electrochemical nature of the fluid above each sensor. When reconstructed, the data can yield an image of the electrochemical signal and the distribution of the signal. Further, repetitive scans of the environment may be used to produce a time lapse, or movie, of the electrochemical signal. Distribution of the signals also provides details about the flow of the signal across the sensor area.

Figure 9:
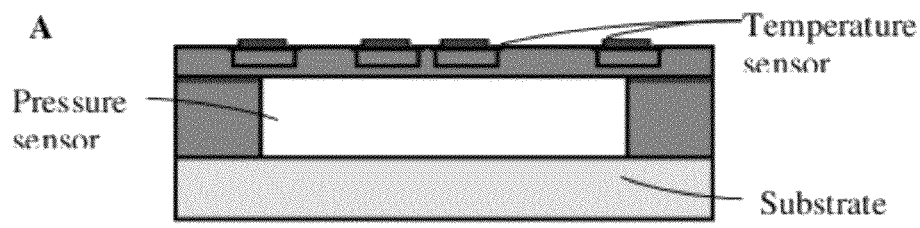
FIG. 9 depicts an array of electrochemical sensors made as a large area sensor flex array.
Figure 9:
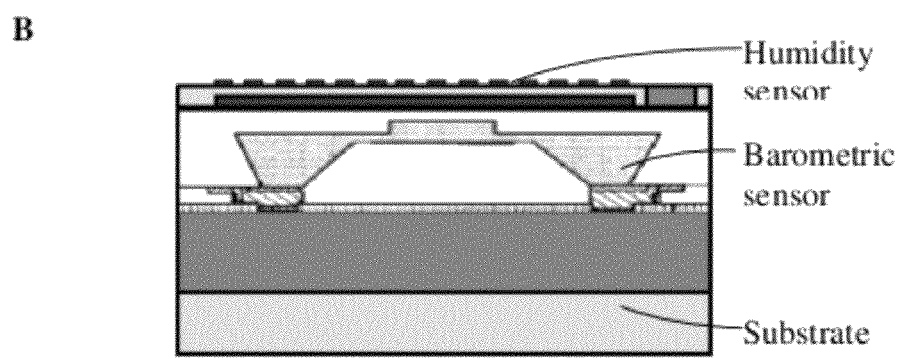

In the fabrication of the monolithic multi-sensor, an SOI wafer was used as the starting material. An epitaxial layer with resistivity of 5 Ω/cm and thickness of about 25 μm was used, which are useful for analog 44 V device process (P. R. Gray and R. G. Mayer, "Analysis and design of analog integrated circuits, Wiley, NY 1990). Piezo resistors by ion implantation and two-layer interconnection by the aluminum are successively formed. Subsequently, the deep silicon etching (ICP-RIE) from backside of the wafer are performed. FIGS. 7 and 9(*a*) and (*b*) show the multisensor pixel sensors, such as sensors comprising the pressure, humidity and temperature sensor (FIG. 9(*b*)). The sensor electronics may be printed on printed circuit board (PCB)-MEMS. Assuming the use of microprocessor with A/D converter such as PIC microchip, the peripheral circuitry amplifies and arranges the sensor outputs into an appropriate electrical level of the 0-5 VDC for the embedded A/D converter. To realize the multi-sensor chip, an SOI bipolar sensor platform with the analog master-slice method was used.

Figure 10:
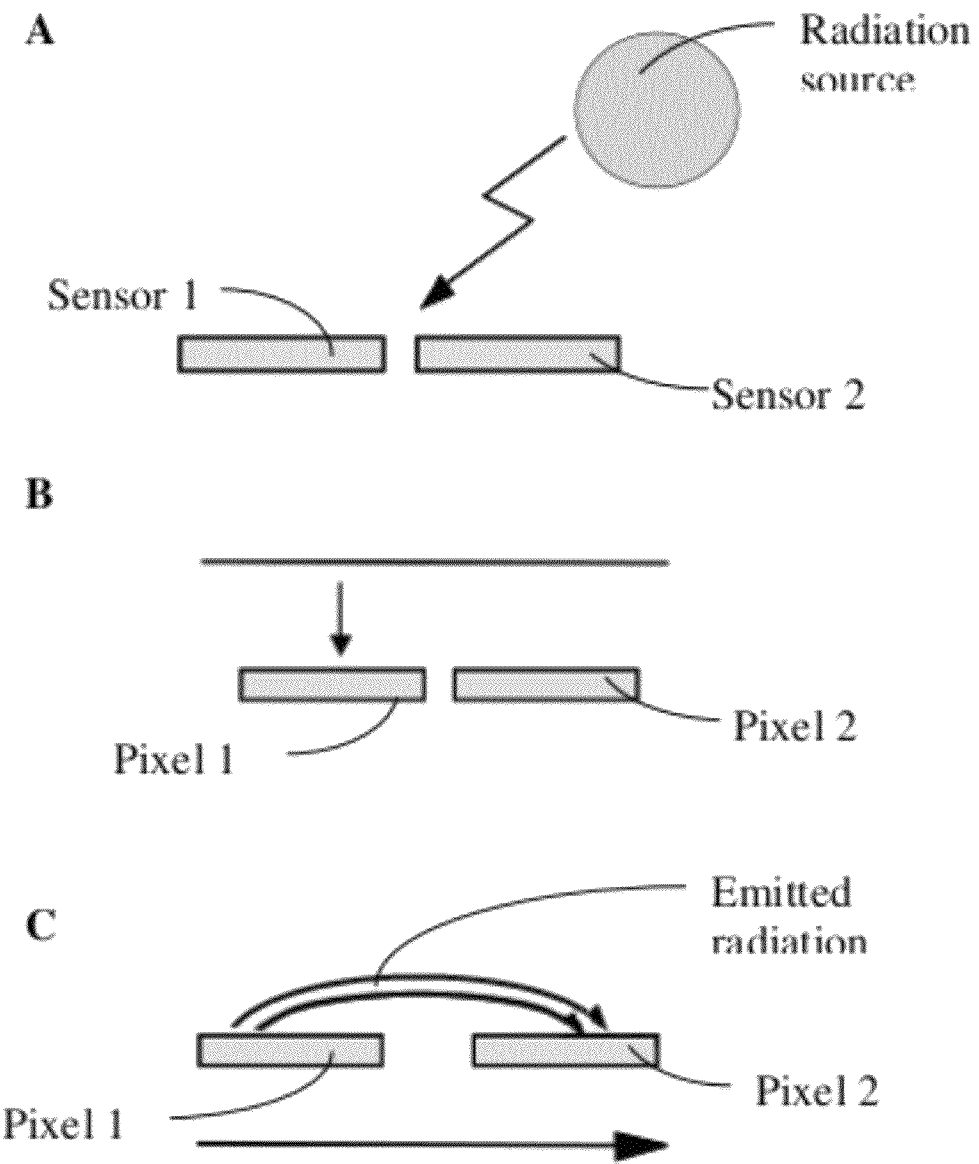
FIGS. 10(*a*) through (*c*) depict detection arrays. (a) A typical imaging array for detecting radiation, such as light or acoustics; whereas (b) proximity and (c) diffusion-limited sensors detect disturbances in self emitted radiation.
Figure 11:
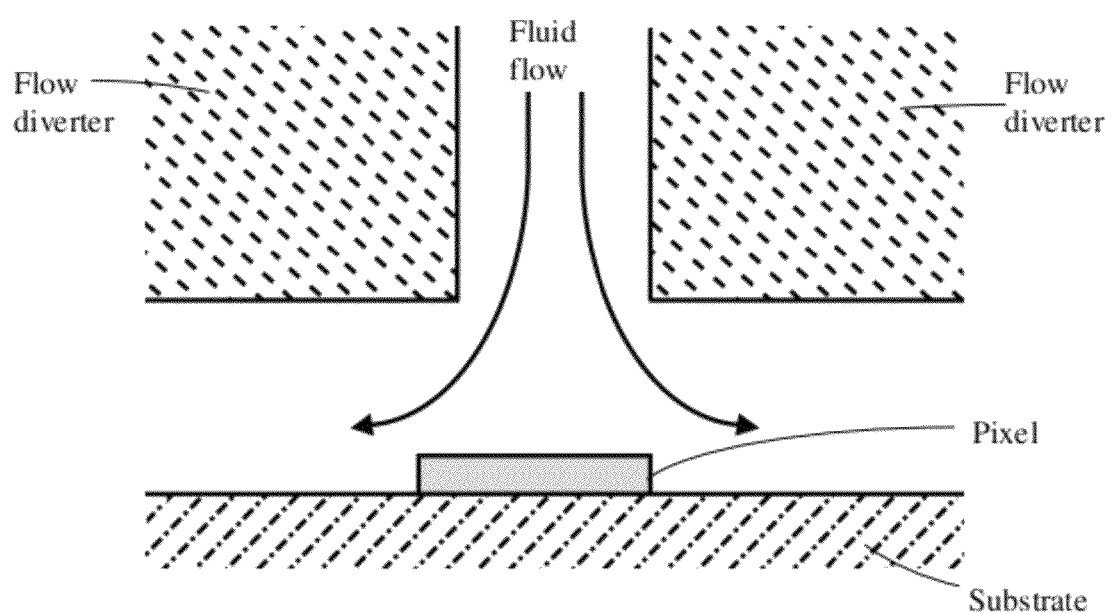
FIG. 11 depicts fluid flow through a flexible PCB array with fluid directors.

Typical imaging arrays detect radiation (light, acoustics) from a distance, as seen in FIG. 10(*a*). The sensor pixels in this invention are designed to resolve proximity/contact (diffusion limited), seen in FIG. 10(*b*), or sensor pixels that detect the disturbance of self emitted radiation, as seen in FIG. 10(*c*). The pixels may be made of many different form factors and in a pattern to sense the physical parameter, chemical and flow. The flow can be assisted, passive or caused by the movement of the pixel array through the media. Since the flexible PCB is amendable to lamination fluid control panels/covers can be placed on top of the sensor array, for better fluid dynamics and control, seen in FIG. 11.

The disclosed device uses several fused sensors integrated as a pixel for environmental monitoring. The multisensor pixel devices utilize an intramodule sensor bus along with an embedded microsystem controller (E. J. Hogenbirk, H. J. Verhoeven, and J. H. Huij sing, "An integrated smart sensor for flow and temperature with I2C bus interface based on thermal sigma-delta modulation," in *Dig. Int. Conf. Solid-State Sensors and Actuators* (*Transducers'93*), Yokohama, Japan, June 1993, pp. 792-79). The microcontroller performs in-module signal processing and permits the microsystem to respond to commands. It also compensates the sensor data and can make in-module decisions based on this data to offload the host system (C. J. Koomen, "Technologies for the multimedia city," in *Proc.* European Solid-State Device Research Conf. (ESSDERC), The Hague, The Netherlands, September 1995, pp. 25-36).

Some embodiments of the sensors use capacitance sensors, which are attractive due to their low power, high sensitivity, and self-test capabilities. This sensor interface chip reads out capacitive devices very quickly, communicates with the microcontroller through the sensor bus, supports self-test and self-calibration, and dissipates low power. The serial data instructions that are transmitted from the MCU over the sensor bus are received, decoded, and stored by the bus interface unit and are applied to control the other circuits. Data written to the interface chip are stored in registers within the bus interface unit. To interface with capacitive sensors, this chip utilizes a low-noise front-end charge integrator to read out the difference between the sensor capacitance and a reference capacitor (Y. E. Park and K. D. Wise, "An MOS switched-capacitor readout amplifier for capacitive pressure sensors," in *Proc. IEEE Custom Integrated Circuits Conf.*, May 1983, pp. 380-384). The interface chip has been fabricated using a standard 3 m single-metal double-poly p-well CMOS process. It dissipates less than 2.2 mW from a single 5 V supply and can resolve input capacitance variations of less than 1 fF with a readout time of 60 s (N. Yazdi, et al, "A low-power generic interface circuit for capacitive sensors," in *Dig. Solid-State Sensor and Actuator Workshop*, Hilton Head Island, S.C., June 1996, pp. 215-218).

The multisensor pixel is a fusion of individual sensor elements into a multisensory pixel, seen in FIGS. 7 and 9. The individual sensors are integrated together such that the different sensor devices are in physical proximity Thus, it is important that each sensor selected may be used in proximity to other sensors. The pixels may be arrays into an imaging panel, and are scalable from micro scale to macroscopic dimensions.

Figure 12:
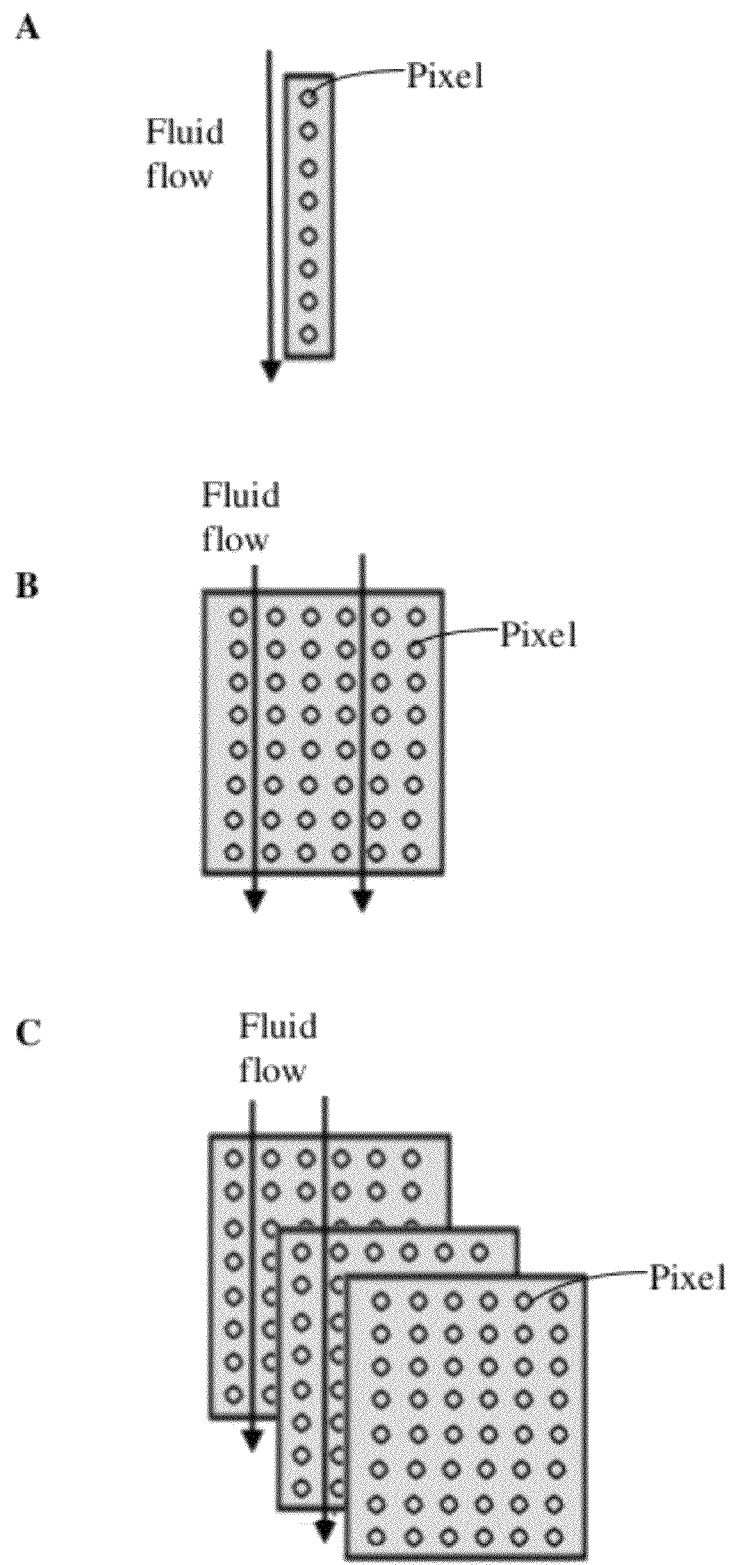
FIG. 12 depicts the scalable nature of the array and dimensional sensing abilities (a) 1 dimensional sensing; (b) 2 dimensional sensing; and (c) 3 dimensional sensing. The circular members represent individual multisensor pixels.
Figure 13:
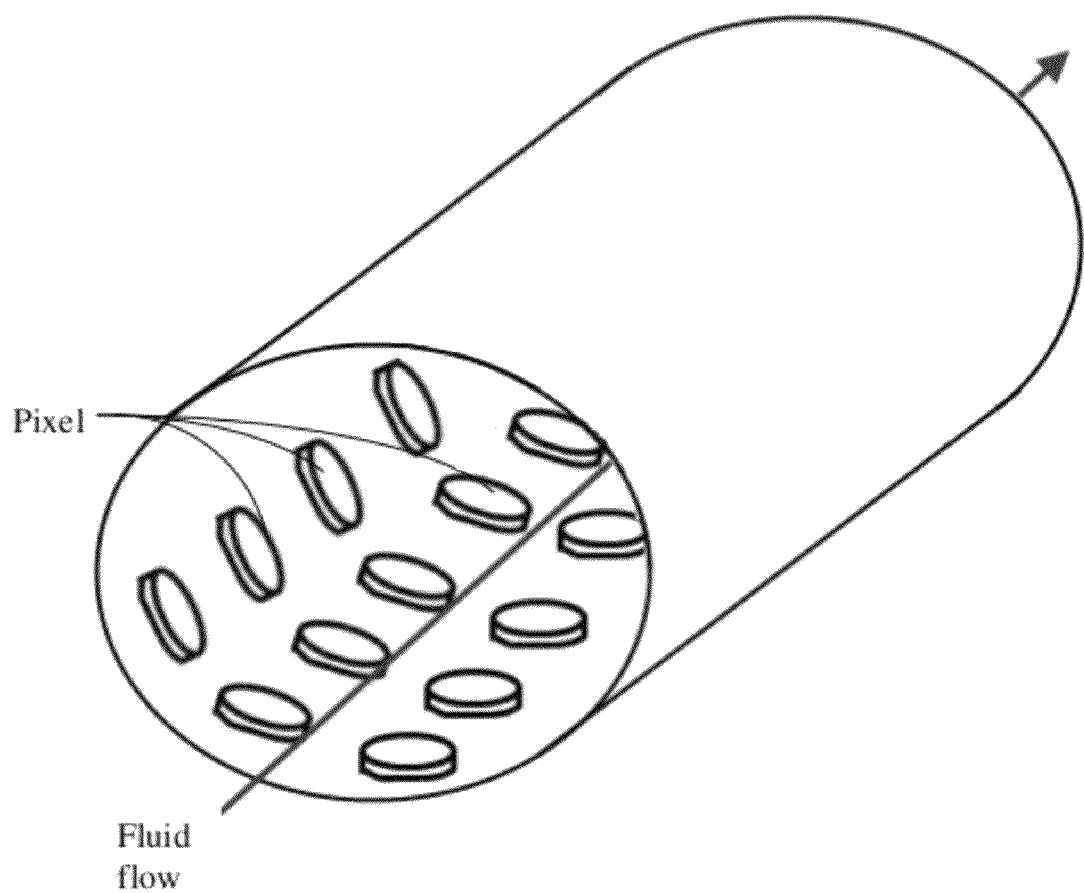
FIG. 13 depicts the sensing element of the invention formed on a tubular imaging sheet. The circular members represent individual multisensor pixels.

Once constructed the flexible panels can be planar or curved 1D, 2D, 3D or nets, as shown in FIGS. 12 and 13

In the preceding specification, all documents, acts, or information disclosed does not constitute an admission that the document, act, or information of any combination thereof was publicly available, known to the public, part of the general knowledge in the art, or was known to be relevant to solve any problem at the time of priority.

The disclosures of all publications cited above are expressly incorporated herein by reference, each in its entirety, to the same extent as if each were incorporated by reference individually.

While there has been described and illustrated specific embodiments of a mutlisensor pixel detection device, it will be apparent to those skilled in the art that variations and modifications are possible without deviating from the broad spirit and principle of the present invention. It is also to be understood that the following claims are intended to cover all of the generic and specific features of the invention herein described, and all statements of the scope of the invention which, as a matter of language, might be said to fall therebetween.

What is claimed is:

1. A multiparameter sensor device, comprising:
    at least two sensor elements fused together, thereby forming a multisensory pixel, wherein the sensor elements are an electrochemical sensor, ion selective electrode, ion detector, polymer sensor, chemical field-effect transistor, chemical sensitive membrane, antibody, luminescent reaction sensor, surface Plasmon element, regenerative reactive sensor, regenerative sense sensor, complementary metal-oxide-semiconductor, surface-on-insulator, liquid crystal polymer, or capacitive sensor;
    wherein at least one multisensory pixel is disposed on at least one face of a circuit board, such that the at least one multisensory pixel is exposed to environmental analytes;
    a control module in electrical communication with the at least one multisensory pixel.

2. The multiparameter sensor device of claim 1, wherein the circuit board is a flexible printed electronics board, a printed circuit board micro-electro-mechanical systems board, a printed circuit board, or a micro-electro-mechanical systems board.

3. The multiparameter sensor device of claim 1, wherein the control module further comprises: a microcontrol unit and input/output interfaces.

4. The multiparameter sensor device of claim 3, wherein the control module further comprises a power management module.

5. The multiparameter sensor device of claim 3, wherein the control module further comprises system memory.

6. The multiparameter sensor device of claim 1, further comprising a battery in electrical communication with the control module and multisensory pixel.

7. The multiparameter sensor device of claim 1, wherein the sensors are adapted to sense environmental conditions selected from the group consisting of temperature, pressure, microbalance, force, humidity, acceleration, and chemical characteristics.

8. The multiparameter sensor device of claim 3, further comprising a transceiver in electrical communication with the input/output interfaces of the control module, wherein the transceiver comprises a silicon bipolar transistor, silicon/silicon-germanium heterojunction bipolar transistor, or GaAs MESFET.

9. A multiparameter sensor camera, comprising:
    at least two sensor elements fused together, thereby forming a multisensory pixel, wherein the sensor elements are an electrochemical sensor, ion selective electrode, ion detector, polymer sensor, chemical field-effect transistor, chemical sensitive membrane, antibody, luminescent reaction sensor, surface Plasmon element, regenerative reactive sensor, regenerative sense sensor, complementary metal-oxide-semiconductor, surface-on-insulator, liquid crystal polymer, or capacitive sensor;
    a camera imaging device comprising a plurality of imaging pixels;
    wherein the imaging pixels of the camera imaging device and the multisensory pixel are integrated as an array on at least one face of a circuit board, such that the imaging pixels are exposed to environmental light source and the at least one multisensory pixel is exposed to environmental analytes;
    a control module in electrical communication with the camera device and the at least one multisensory pixel.

10. The multiparameter sensor camera of claim 9, further comprising a plurality of multiparameter pixels disposed as an array.

11. The multiparameter sensor camera of claim 9, wherein the array is disposed on a flexible printed electronics board or a printed circuit board micro-electro-mechanical systems board.

12. The multiparameter sensor camera of claim 9, wherein the control module further comprises: a microcontrol unit and input/output interfaces.

13. The multiparameter sensor camera of claim 12, wherein the control module further comprises a power management module.

14. The multiparameter sensor camera of claim 12, wherein the control module further comprises system memory.

15. The multiparameter sensor camera of claim 9, further comprising a battery in electrical communication with the control module and multisensory pixel.

16. The multiparameter sensor camera of claim 9, wherein the sensors are adapted to sense environmental conditions selected from the group consisting of temperature, pressure, microbalance, force, humidity, acceleration, and chemical characteristics.

17. The multiparameter sensor camera of claim 12, further comprising a transceiver in electrical communication with the input/output interfaces of the control module, wherein the transceiver comprises a silicon bipolar transistor, silicon/silicon-germanium heterojunction bipolar transistor, or GaAs MESFET.

18. The multiparameter sensor camera of claim 9, wherein the imaging pixels are CMOS sensors.

* * * * *